US00PP30730P2

(12) United States Plant Patent
Bacon

(10) Patent No.: US PP30,730 P2
(45) Date of Patent: Jul. 23, 2019

(54) CHERRY TREE NAMED 'SUCHERRYONE'

(50) Latin Name: ***Prunus avium* L.**
Varietal Denomination: Sucherryone

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 15/932,174

(22) Filed: Feb. 15, 2018

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
See application file for complete search history.

*Primary Examiner* — Susan McCormick Ewoldt
(74) *Attorney, Agent, or Firm* — Knobbe, Martens, Olson & Bear, LLP

(57) ABSTRACT

A new and distinct cherry tree variety, *Prunus avium* L., cv. 'Sucherryone' is characterized by very early ripening, large-size fruit, reniform fruit shape and high acidity.

1 Drawing Sheet

Latin name of the genus and species claimed: *Prunus avium* L.

Variety denomination: 'Sucherryone'

BACKGROUND AND SUMMARY OF THE INVENTION

This invention relates to the discovery and asexual propagation of a new and distinct variety of cherry, *Prunus avium* L. 'Sucherryone'. The new variety was first selected in May 2007 by Terry Bacon as breeder number 'CH827'. The new variety was first evaluated by Terry Bacon near Wasco, Calif. in Kern County. The variety 'Sucherryone' was originated by hybridization.

The new variety 'Sucherryone' is characterized by very early ripening, large-size fruit, reniform fruit shape and high acidity.

The seed parent is 'Brooks' (unpatented), and it was open pollinated. The parent varieties were first crossed in February 2003, with the date of first sowing being February 2004 and the date of first flowering being February 2007. The new cherry variety 'Sucherryone' was first asexually propagated by Terry Bacon near Wasco, Kern County, Calif. in January 2013 by dormant grafting.

The new variety 'Sucherryone' is similar to its seed parent, 'Brooks' in that they both have similar shaped fruit, but the bloom of the new variety 'Sucherryone' starts 9 days earlier than for 'Brooks' and harvest starts about 9 days earlier than for 'Brooks'. The new variety 'Sucherryone' also differs from 'Brooks' in that the chilling requirement is 750 chill units compared to 850 chill units for 'Brooks'.

The harvest of the fruit of the new variety 'Sucherryone' starts about 8 days earlier than 'Tulare' (unpatented) and the fruit shape of the new variety is reniform compared to cordate for 'Tulare'. The new variety 'Sucherryone' also differs from 'Tulare' in that the chilling requirement is 750 chill units compared to 800 chill units for 'Tulare'.

The new variety 'Sucherryone' has a similar fruit shape as 'Bing' (unpatented), but the harvest of the new variety 'Sucherryone' starts about 14 days earlier than that of 'Bing'. The frequency of double pistils in the new variety 'Sucherryone' is rare compared to frequent for 'Bing'. The harvest of the new variety 'Sucherryone' starts at about the same time as that of 'Minnie Royal' (PP12,942), but the fruit shape of the new variety is reniform compared to cordate for 'Minnie Royal'. The new variety 'Sucherryone' also differs from 'Minnie Royal' in that the chilling requirement for 'Sucherryone' is 750 chill units compared to 650 chill units for 'Minnie Royal'.

The new variety 'Sucherryone' has been shown to maintain its distinguishing characteristics through successive asexual propagations by, for example, cuttings and grafting onto 'Wieroot 158' (unpatented) rootstock.

BRIEF DESCRIPTION OF THE DRAWING

The accompanying color photographic illustration shows typical specimens of the foliage and fruit of the present new grape variety 'Sucherryone'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to 8 year old 'Sucherryone' trees grown in the vicinity of Wasco, Kern County, Calif. during 2017, and is believed to apply to plants of the variety grown under similar conditions of soil and climate elsewhere.

TREE

General: (Measurements taken on 8 year old trees unless otherwise noted.)

*Size.*—Medium. Reaches a height of approximately 3 meters with normal pruning.
*Vigor.*—Strong. Top shoot growth of about 1.5 meters during the first growing season.
*Growth.*—Semi-upright.
*Productivity.*—Productive. Produces ample fruit set annually.
*Fertility.*—Self-incompatible; pollinator required.
*Hardiness.*—Hardy in all fruit growing areas of California. Winter chilling requirement is approximately 750 hours at or below 7.2° C.
*Disease resistance/susceptibility.*—No specific testing for relative plant disease resistance/susceptibility has been undertaken. Under close observation in Kern County, Calif., no particular plant/fruit disease resistance/susceptibility has been observed.

Trunk: (Measurements at approximately 30 cm above the soil line.)
*Diameter.*—Approximately 25 cm.
*Texture.*—Medium shaggy; increases with age of tree.
*Trunk color.*—About Light Black 202C with highlights of Dark Greyed-Orange 176B, becoming darker with age.

Branches: (Measurements at approximately 90 cm above the soil line.)
*Diameter.*—Approximately 13 cm.
*Texture.*—Medium shaggy; increasing with tree age.
*Color.*—About Light Black 202C with highlights of Medium Greyed-Orange 176C, becoming darker with age.
*Lenticels density.*—Approximately 0-2 per $cm^2$.
*Lenticels color.*—About Medium Greyed-Green 198B.
*Lenticels length.*—Approximately 10 mm.
*Lenticels width.*—Approximately 3 mm.

Shoots: (Data taken in May at the midpoint of current-season growth.)

Young shoots:
*Anthocyanin coloration of apex (during raping growth).*—Weak.
*Pubescence of apex during rapid growth.*—Medium.

Current season shoots:
*Thickness at midlength.*—Medium; approximately 7 mm.
*Length of internodes.*—Normal; mostly 2 cm.
*Color topside.*—About Light Green 138C.
*Color underside.*—About Light Green 138C.
*Lenticels density.*—Few; about 1 per $cm^2$.
*Lenticels color.*—About Medium Greyed-Green 198B.
*Lenticel dimensions.*—Width: Approximately 1 mm. Length: Approximately 2 mm.
*Presence of anthocyanin coloration.*—Absent or very sparse.

One year old shoots:
*Number of flower buds per spur.*—About 10, varies from 3 to 12.

FOLIAGE

Leaves: (Data taken in September at the midpoint of current-season growth)
*Average length.*—Medium; approximately 11 cm without petiole.
*Average width.*—Medium; approximately 4.5 cm.
*Length:width ratio.*—Medium; about 2.4:1.
*Shape.*—Elliptic.
*Color of upper side and intensity.*—Medium intensity; about Dark Green 136B.
*Color of lower side.*—About Light Green 138C.
*Angle at base.*—Rounded.
*Angle at apex.*—Acuminate.
*Vein color.*—About Light Green 139D.
*Presence of red coloration of mid-vein on the lower side.*—Absent.
*Surface texture.*—Smooth on both top and bottom surfaces.
*Shape in the cross section.*—Slightly up-folded.
*Leaf blade tip.*—In the plane of the leaf.
*Undulation of margin.*—Slight.
*Margin.*—Shallow serrate.
*Ratio length of leaf blade:length of petiole.*—Medium: 3.7:1.
*Venation.*—Pinnately veined.

Petiole:
*Average length.*—Medium; approximately 30 mm.
*Average diameter.*—Approximately 2 mm.
*Color.*—About Medium Green 139C.

Stipules:
*Number/leaf bud.*—Usually 2.
*Typical length.*—Approximately 11 mm.
*Color.*—About Dark Greyed-Orange 166A when dried.
*Persistence.*—Falls off.

Glands (Nectaries):
*Form.*—Reniform.
*Average number and arrangement.*—Usually 2, alternating. Predominately on petiole.
*Dimension.*—Approximately 2 mm long by 1.4 mm wide.
*Color.*—About Dark Greyed-Red 178B in September.

Vegetative buds: (Data taken in September at midpoint of current-season growth)
*Bud dimensions.*—Approximately 10 mm long by 4 mm wide.
*Bud shape.*—Conical.
*Color.*—About Dark Greyed-Orange 177A.

FLOWERS

General:
*Type of bloom.*—Showy.
*Diameter of fully opened flower.*—Approximately 28 mm.
*Flower aroma.*—Medium-strong.
*Time of beginning of flowering.*—Approximately March 7.
*Flower blooming period.*—First Bloom: Approximately March 7. Full Bloom: Approximately March 11.
*Location of first bloom.*—Tips of one-year-old shoots.
*Location of full bloom.*—Central part of the tree canopy.
*Duration of bloom.*—Approximately 10 days.

Flower buds: (Data taken in September at midpoint of current-season growth)
*Bud dimensions.*—Approximately 8 mm long by 3 mm wide.
*Bud shape.*—Conical.
*Color.*—About Dark Greyed-Orange 177B.
*Number of flowers per flower bud.*—Average 4; varies from 2 to 5.

*Number of buds per spur.*—Average 7; varies from 5 to 9.

Pedicels:

*Length.*—Approximately 12 mm.

*Color.*—About Medium Green 138B.

Sepals:

*Number.*—5.

*Shape.*—Triangular.

*Position.*—Adpressed to petals, alternate with petals.

*Length.*—Approximately 7 mm.

*Width.*—Approximately 5 mm.

*Surface texture.*—Glabrous on outer and inner surfaces.

*Color.*—About Dark Greyed-Purple 184A.

Petals:

*Number.*—5.

*Arrangement.*—Usually free.

*Color.*—About White 155A.

*Surface texture.*—Smooth on upper and lower surface.

*Dimensions.*—Approximately 16 mm long by 14 mm wide.

*Shape.*—Circular.

*Apex shape.*—Rounded.

*Base shape.*—Narrows at point of attachment.

*Undulation of margins.*—Slightly undulating.

*Frequency of flowers with double petals.*—Rare.

Stigma:

*Position compared to anthers.*—Slightly higher.

Stamens:

*Number.*—About 38; varies from 34 to 40.

*Filament length.*—Average 12 mm.

*Filament color.*—About White 155A.

*Pollen.*—Present.

*Flower pollen color.*—About Light Yellow 3D.

Pistil:

*Length.*—Approximately 16 mm.

*Surface.*—Glabrous.

*Frequency of supplementary pistils.*—Rare.

FRUIT

General: (Description taken at firm-mature near Wasco, Kern County, Calif).

*Date of first pick.*—Approximately April 28.

*Date of last pick.*—Approximately May 8.

*Time of beginning of fruit ripening.*—Very early.

Stem:

*Length.*—Medium, approximately 24 mm.

*Thickness.*—Medium, approximately 2 mm.

*Color.*—About Light Green 139D.

*Abscission layer between stalk and fruit.*—Absent.

Fruit size:

*Size.*—Large.

*Weight.*—About 8 g.

*Height.*—About 22 mm.

*Diameter perpendicular to suture.*—Approximately 24 mm.

*Diameter ventral side, facing suture.*—Approximately 26 mm.

Fruit shape:

*Shape viewed from apex.*—Circular.

*Shape ventral side, facing suture.*—Reniform.

*Symmetry viewed from pistil end.*—Symmetric or slightly asymmetric.

*Shape of pistil end.*—Slightly depressed.

*Depth of stem cavity.*—Medium, about 1.8 mm.

*Width of stem cavity.*—Medium, about 4 mm.

*Promenence of suture.*—Absent or very weakly conspicuous.

Fruit skin:

*Thickness.*—Intermediate, typical of most varieties.

*Adherence to flesh.*—Strong.

*Taste.*—Neutral.

*Surface texture.*—Smooth.

*Bloom.*—Wanting.

*Tendency to crack.*—None during dry weather. Slight tendency to crack in wet weather but varies with stage of maturity.

*Number of lenticels on skin.*—Medium, approximately 12 per $cm^2$.

*Color.*—About Medium Red 46B, becoming Dark Purple 79A.

Flesh:

*Ripens.*—Evenly.

*Color.*—At full maturity about Dark Red 53B to Dark Red 53A.

*Color of juice.*—About Light Red 53D at full maturity.

*Flavor.*—Mildly tart-sweet.

*Firmness.*—Firm; comparable to most commercial varieties.

*Juiciness.*—Medium; able to squeeze free juice easily.

*Sweetness.*—Medium; about 17% brix at harvest.

*Acidity.*—High for cherries; about 0.82% titratable acidity.

*Texture.*—Firm.

*Fibers.*—Few, small and tender.

Stone:

*Stone size.*—Medium. Length: Approximately 9 mm. Diameter Facing Suture: Approximately 6 mm. Diameter Perpendicular to Suture Plane: Approximately 9 mm.

*Ratio weight of fruit:weight of stone.*—Medium, about 53:1.

*Color.*—About Medium Greyed-Yellow 161C when dried.

*Shape in lateral view perpendicular to suture.*—Circular.

*Shape in ventral view facing suture.*—Broad elliptic.

*Shape in basal view.*—Broad elliptic.

*Base shape.*—Flat.

*Apex shape.*—Rounded.

*Ridges.*—A small narrow ridge on each side of suture, extending from base to apex.

*Symmetry in lateral view.*—Symmetric or slightly asymmetric.

*Surface.*—Nearly smooth except for small ridges near the suture.

*Width of stalk end.*—Narrow, approximately 1 mm.

*Tendency to split.*—None.

*Adherence to flesh.*—Semi-freestone.

Market:

*Use.*—Dessert.

*Market.*—Local and long distance.

*Storage quality.*—Good, held well for 3 weeks in cold storage at 33° F. and maintained good appearance and eating quality.

*Shipping quality.*—Good, showed minimal bruising or scarring during harvest, packing and shipping trials.

What is claimed is:

1. A new and distinct variety of cherry tree as herein described and illustrated.

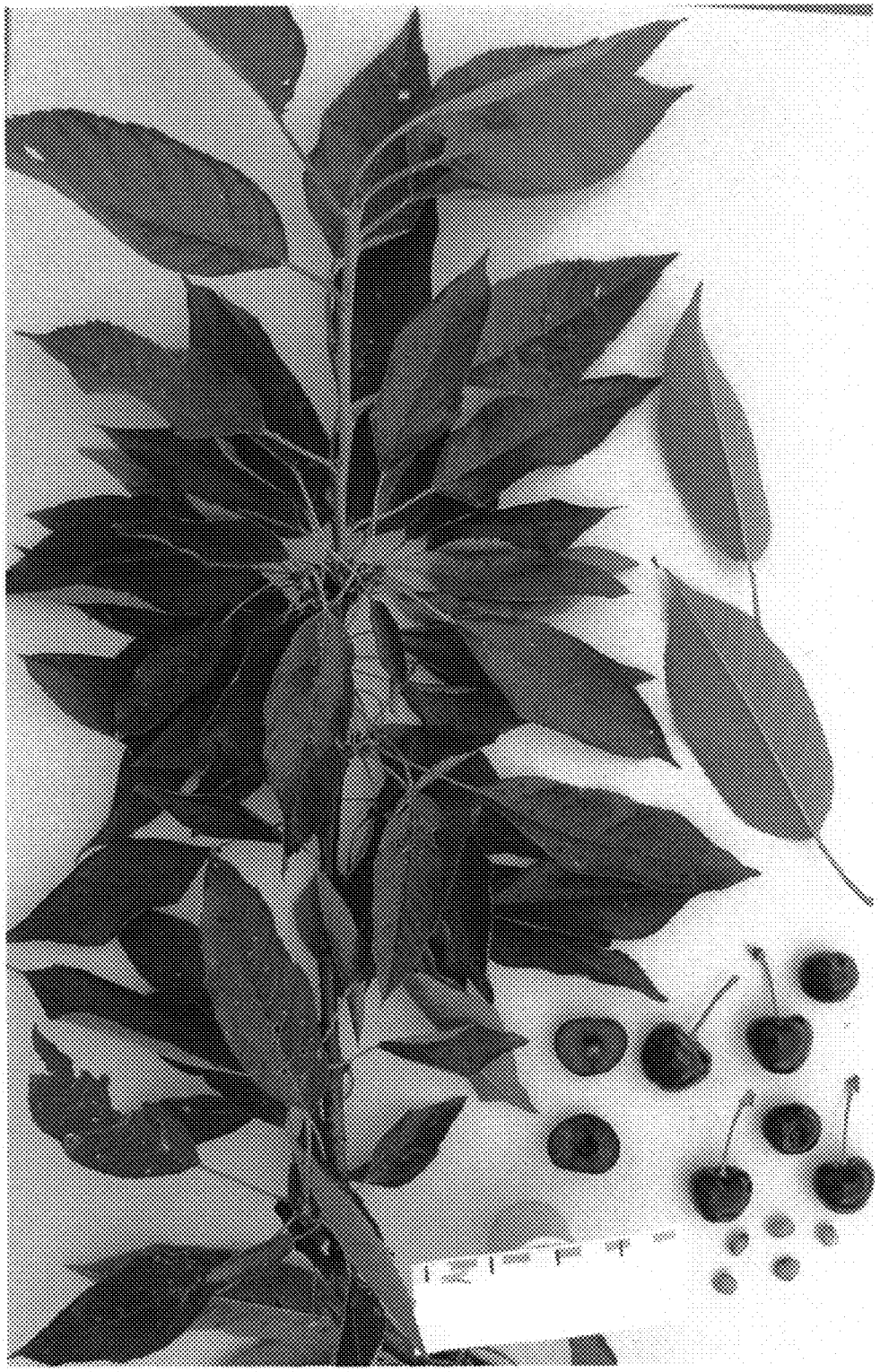

* * * * *